United States Patent
Govari

(10) Patent No.: US 11,006,886 B2
(45) Date of Patent: May 18, 2021

(54) VISUALIZATION OF DIFFERENT CARDIAC RHYTHMS USING DIFFERENT TIMING-PATTERN DISPLAYS

(71) Applicant: Biosense Webster (Israel) Ltd., Yokneam (IL)

(72) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 152 days.

(21) Appl. No.: 16/227,367

(22) Filed: Dec. 20, 2018

(65) Prior Publication Data
US 2020/0196889 A1    Jun. 25, 2020

(51) Int. Cl.
| A61B 5/341 | (2021.01) |
| A61B 5/00 | (2006.01) |
| A61B 5/283 | (2021.01) |
| A61B 5/335 | (2021.01) |
| A61B 5/339 | (2021.01) |
| A61B 5/364 | (2021.01) |

(52) U.S. Cl.
CPC .............. *A61B 5/341* (2021.01); *A61B 5/283* (2021.01); *A61B 5/335* (2021.01); *A61B 5/339* (2021.01); *A61B 5/364* (2021.01); *A61B 5/7264* (2013.01); *A61B 5/7425* (2013.01)

(58) Field of Classification Search
CPC . A61B 5/04011; A61B 5/04012; A61B 5/042; A61B 5/04325; A61B 5/044; A61B 5/0468; A61B 5/7264; A61B 5/7425; A61B 5/283; A61B 5/335; A61B 5/339; A61B 5/341; A61B 5/364
See application file for complete search history.

(56) References Cited

U.S. PATENT DOCUMENTS

| 5,687,737 A | * | 11/1997 | Branham | ............ A61B 5/0422 600/523 |
| 8,456,182 B2 | | 6/2013 | Bar-Tal et al. | |
| 9,314,179 B1 | * | 4/2016 | Brodnick | ............... A61B 5/725 |
| 9,974,462 B2 | | 5/2018 | Jayan et al. | |

(Continued)

OTHER PUBLICATIONS

Anan T et al: "Arrhythmia analysis by successive RR plotting", Journal of Electrocardiology, Elsevier Science, XX, vol. 23, No. 3, Jul. 1, 1990 (Jul. 1, 1990), pp. 243-248, XP022997324, ISSN: 0022-0736, DOI: 10.1016/0022-0736(90)90163-V [retrieved on Jul. 1, 1990].

(Continued)

*Primary Examiner* — Christopher A Flory
(74) *Attorney, Agent, or Firm* — Scully, Scott, Murphy & Presser, PC

(57) ABSTRACT

A method includes receiving an electrocardiogram (ECG) measured at a given location over a portion of a heart. Based on the measured ECG, a rhythmic pattern is identified over a given time-interval. The rhythmic pattern corresponds to a relation between a present cardiac cycle length and a preceding cardiac cycle length. Based on the identified rhythmic pattern, a classification of the location as either showing regular pattern or showing arrhythmia is determined. The location is graphically encoded according to the classification. The graphically encoded location is overlaid on an anatomical map of the portion of a heart.

10 Claims, 3 Drawing Sheets

(56) References Cited

U.S. PATENT DOCUMENTS

| | | | | |
|---|---|---|---|---|
| 2003/0023130 A1* | 1/2003 | Ciaccio | A61B 5/04011 | 600/12 |
| 2004/0059237 A1* | 3/2004 | Narayan | A61B 5/04525 | 600/509 |
| 2004/0243012 A1* | 12/2004 | Ciaccio | A61B 18/1492 | 600/509 |
| 2007/0021679 A1* | 1/2007 | Narayan | A61N 1/3625 | 600/518 |
| 2008/0199048 A1* | 8/2008 | Eck | G06T 7/38 | 382/107 |
| 2010/0204552 A1* | 8/2010 | Yamamoto | A61B 5/0404 | 600/301 |
| 2011/0251505 A1 | 10/2011 | Narayan et al. | | |
| 2012/0184863 A1* | 7/2012 | Harlev | A61B 18/00 | 600/509 |
| 2012/0184864 A1* | 7/2012 | Harlev | G16H 15/00 | 600/509 |
| 2012/0184865 A1* | 7/2012 | Harlev | A61B 5/743 | 600/509 |
| 2013/0109945 A1* | 5/2013 | Harlev | A61B 5/743 | 600/374 |
| 2014/0288451 A1* | 9/2014 | Brodnick | A61B 5/04012 | 600/509 |
| 2014/0330145 A1* | 11/2014 | Brodnick | A61B 5/0422 | 600/509 |
| 2015/0112178 A1* | 4/2015 | Harlev | A61B 5/04012 | 600/374 |
| 2015/0126841 A1* | 5/2015 | Ghosh | A61B 5/0422 | 600/374 |
| 2016/0051160 A1* | 2/2016 | Harlev | A61B 5/0536 | 600/374 |
| 2016/0073913 A1* | 3/2016 | Francis | A61B 5/04011 | 600/374 |
| 2016/0089048 A1 | 3/2016 | Brodnick et al. | | |
| 2016/0089050 A1 | 3/2016 | Thakur et al. | | |
| 2017/0042436 A1* | 2/2017 | Harlev | A61B 18/00 | |
| 2017/0055863 A1* | 3/2017 | Baumann | A61B 5/7282 | |
| 2017/0209059 A1* | 7/2017 | Nabutovsky | A61B 5/1102 | |
| 2017/0281033 A1 | 10/2017 | Higgins | | |
| 2018/0296167 A1* | 10/2018 | Stewart | A61B 5/0422 | |
| 2019/0298272 A1* | 10/2019 | Persen | A61B 5/02416 | |

OTHER PUBLICATIONS

Extended European Search Report dated Feb. 14, 2020 from related EP 19 21 7872.

\* cited by examiner

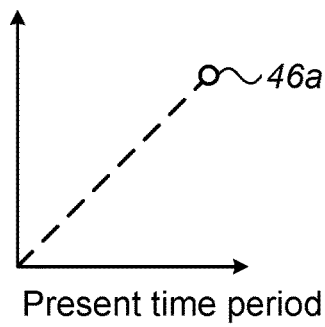
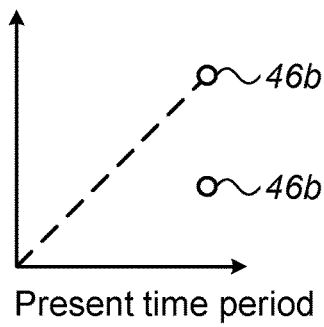
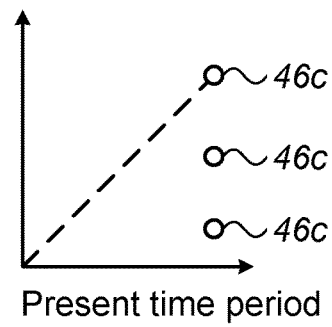
FIG. 2A     FIG. 2B     FIG. 2C
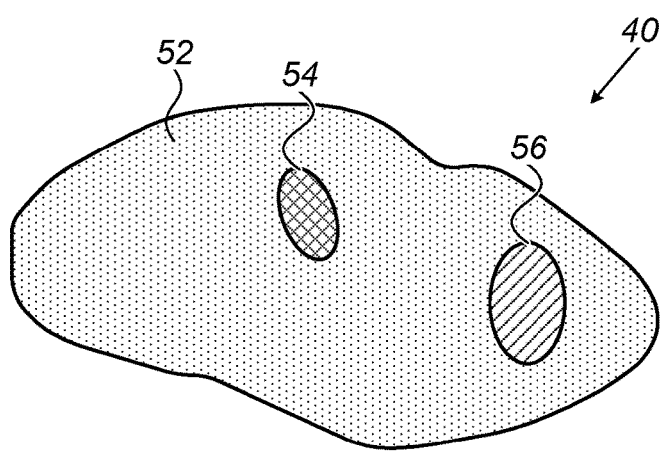
FIG. 3

VISUALIZATION OF DIFFERENT CARDIAC RHYTHMS USING DIFFERENT TIMING-PATTERN DISPLAYS

FIELD OF THE INVENTION

The present invention relates generally to electro-anatomical mapping, and particularly to methods and systems for cardiac electro-anatomical mapping.

BACKGROUND OF THE INVENTION

Techniques for electro-anatomical mapping of cardiac chambers were previously discussed in the patent literature. For example, U.S. Patent Application Publication 2016/0089048 describes an automatic method of determining local activation time (LAT) from at least four multichannel cardiac electrogram signals including a ventricular channel, a mapping channel and a plurality of reference channels. The method comprises (a) storing the cardiac channel signals, (b) using the ventricular and mapping channel signals and a first reference channel signal to compute LAT values at a plurality of mapping-channel locations, (c) monitoring the timing stability of the first reference channel signal, and (d) if the timing stability of the monitored signal falls below a stability standard, using the signal of a second reference channel to determine LAT values. Substantial loss of LAT values is avoided in spite of loss of timing stability.

As another example, U.S. Patent Application Publication 2016/0089050 describes an anatomical mapping system and method includes mapping electrodes that are configured to detect activation signals of cardiac activity. A processing system is configured to record the detected activation signals and generate a vector field for each sensed activation signal during each instance of the physiological activity. The processing system determines an onset time and alternative onset time candidates, identifies an initial vector field template based on a degree of similarity between the initial vector field and a vector field template from a bank of templates, then determines an optimized onset time for each activation signal based on a degree similarity between the onset time candidates and initial vector field template.

U.S. Patent Application Publication 2011/0251505 describes system, assembly and method to facilitate reconstruction of cardiac information representing a complex rhythm disorder associated with a patient's heart to indicate a source of the heart rhythm disorder. The complex rhythm disorder can be treated by application of energy to modify the source of the rhythm disorder.

SUMMARY OF THE INVENTION

An embodiment of the present invention provides a method including receiving an electrocardiogram (ECG) measured at a given location over a portion of a heart. Based on the measured ECG, a rhythmic pattern is identified over a given time-interval. The rhythmic pattern corresponds to a relation between a present cardiac cycle length and a preceding cardiac cycle length. Based on the identified rhythmic pattern, a classification of the location as either showing regular pattern or showing arrhythmia is determined. The location is graphically encoded according to the classification. The graphically encoded location is overlaid on an anatomical map of the portion of a heart.

In some embodiments, identifying the rhythmic pattern includes calculating a difference between the present cardiac cycle length and the preceding cardiac cycle length.

In some embodiments, classifying the location as showing arrhythmia includes classifying a type of the arrhythmia.

In an embodiment, overlaying the graphically encoded location includes generating a spatiotemporal electro-anatomical map of the portion of a heart. In another embodiment, the method further includes measuring the ECG using a catheter-based system for electro-anatomical mapping.

There is additionally provided, in accordance with an embodiment of the present invention, a system including a memory and a processor. The memory is configured to store an electrocardiogram (ECG) measured at a given location over a portion of a heart. The processor is configured to identify, based on the measured ECG, a rhythmic pattern over a given time-interval. The rhythmic pattern corresponds to a relation between a present cardiac cycle length and a preceding cardiac cycle length. The processor is additionally configured to determine, based on the identified rhythmic pattern, a classification of the location as either showing regular pattern or showing arrhythmia. The processor is further configured to graphically encode the location according to the classification, and overlay the graphically encoded location on an anatomical map of the portion of a heart.

The present invention will be more fully understood from the following detailed description of the embodiments thereof, taken together with the drawings in which:

BRIEF DESCRIPTION OF THE DRAWINGS

FIGS. 2A-2C are schematic, illustrative scatterplots of local heartbeat timing patterns, in accordance with an embodiment of the present invention;

FIG. 3 is a schematic, pictorial illustration of a spatiotemporal electro-anatomical map of a cardiac chamber, in accordance with an embodiment of the present invention.

DETAILED DESCRIPTION OF EMBODIMENTS

Overview

Figure 1:
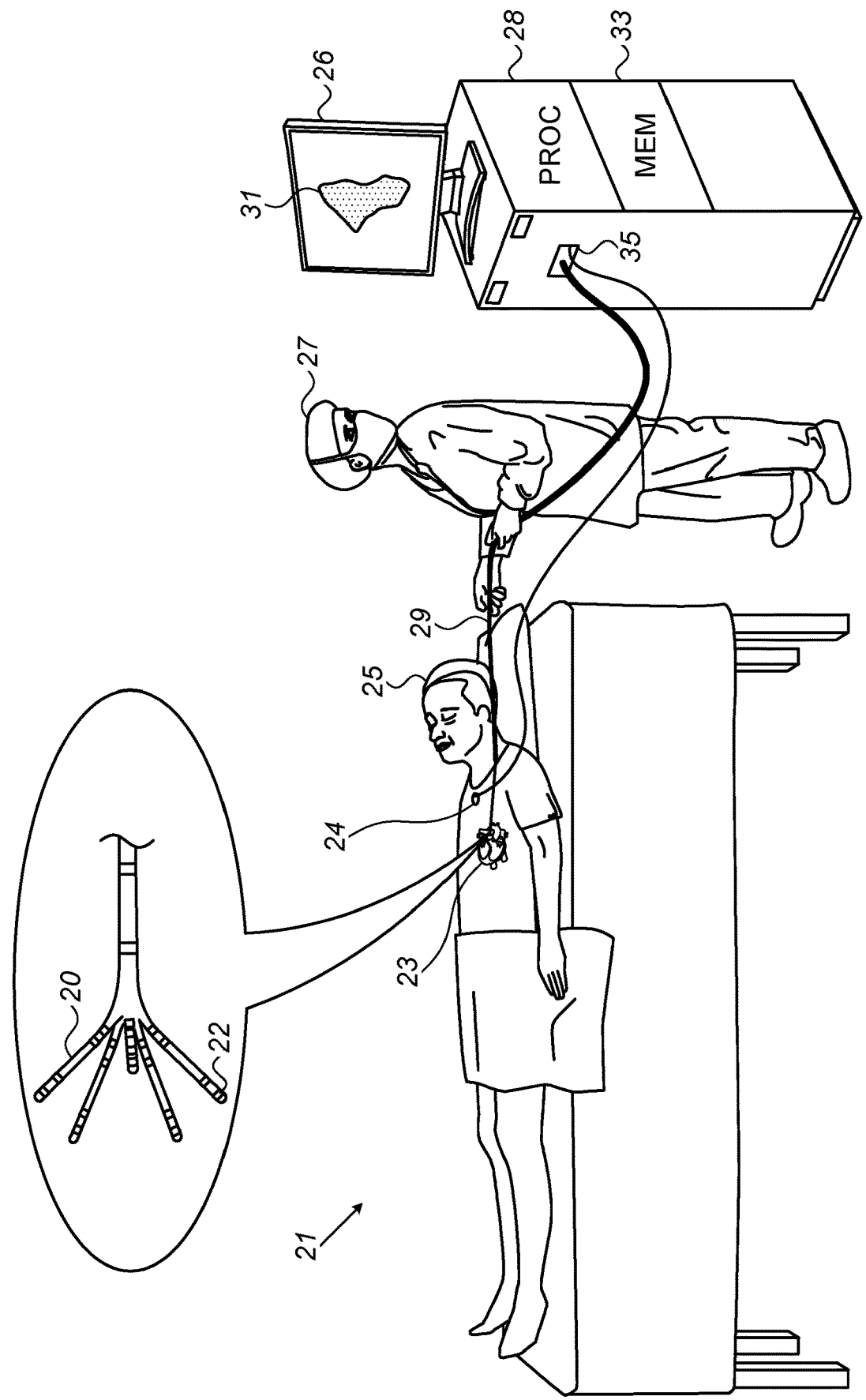
FIG. 1 is a schematic, pictorial illustration of a system for electro-anatomical mapping, in accordance with an embodiment of the present invention.

One important use of catheter-based electro-anatomical mapping procedures is to identify intra-cardiac tissue locations that serve as potential origins or conduction paths for an arrhythmia. For diagnosis, a certain tissue location may be characterized as normal or aberrant based on analyzing a rhythmic pattern of electrophysiological (EP) activity that the catheter records at the location.

Such locally recorded rhythmic patterns, seen, for example, in intra-cardiac electrocardiograms (ECG), can be concisely expressed by a property of a cardiac cycle length (i.e., periodicity) of the cardiac EP activation. A repeatable cycle length, usually meaning a normal sinus rhythm, indicates a healthy and normal cardiac tissue location. On the other hand, a highly variable cycle length indicates an aberrant tissue location, from which an arrhythmia originates, or through which it propagates.

At present, a physician may analyze an electro-anatomical map of a heart chamber by manually examining different regions of the heart chamber to try to identify an origin and/or a path of an arrhythmia. This sort of examination, however, requires meticulous work that is laborious and time consuming.

Embodiments of the present invention that are described hereinafter generate a spatiotemporal electro-anatomical map (also named hereinafter "spatiotemporal EP map") of surface tissue of a portion of a heart, such as of a cardiac chamber. The spatiotemporal EP map graphically encodes tissue locations as healthy or aberrant. Furthermore, the disclosed technique for generating the spatiotemporal EP map can identify and encode different types of arrhythmic behaviors.

The disclosed spatiotemporal EP map is produced by classifying timing patterns exhibited by tissue locations over a portion of the heart, such as those exhibited over a cardiac chamber wall tissue. A timing pattern is identified, for any particular tissue location, by a processor comparing a "present" time period, i.e., cycle length, against a preceding, or "previous," time period. The timing pattern may be identified by the processor over a typical time-interval of several seconds. In this way, a timing pattern of a tissue location is indicative of the rhythmic pattern at the location.

Tissue locations that exhibit normal sinus rhythm (e.g., with a heart beat rate that is repeatable enough over several seconds) yield a timing pattern that essentially gives a single point, as described below. However, tissue locations that exhibit arrhythmia will generate timing patterns different from the sinus pattern, and each different type of arrythmia will typically have a distinct characteristic timing pattern, as shown below.

In some embodiments, a memory is provided, which is configured to store an electrocardiogram (ECG) measured at a given location over a portion of a heart. A processor is configured to (a) based on the measured ECG, identify a rhythmic pattern over a given time-interval, the rhythmic pattern corresponding to a relation between a present cardiac cycle length and a preceding cardiac cycle length, and (b) based on the identified rhythmic pattern, determine a classification of the location as either showing regular pattern (i.e., normal) or showing arrhythmia. The processor is further configured to graphically encode the location according to the classification, and to overlay the graphically encoded location on an anatomical map of the portion of a heart.

In an embodiment, the processor overlays the encoding with the different timing patterns of locations on an anatomical map of the cardiac chamber to create a spatiotemporal map of the cardiac chamber, and the spatiotemporal map can assist the physician in locating an origin of an arrythmia and/or indicate the arrythmia type.

Typically, the processor is programmed in software containing a particular algorithm that enables the processor to conduct each of the processor related steps and functions outlined above.

The disclosed spatiotemporal electro-anatomical mapping technique provides the physician with a clear visual representation of normal versus aberrant regions of a cardiac chamber tissue and may thus facilitate an easier diagnosis of, and treatment-selection for, an arrythmia.

System Description

FIG. 1 is a schematic, pictorial illustration of a system for electro-anatomical mapping, in accordance with an embodiment of the present invention. FIG. 1 depicts a physician 27 using an electro-anatomical catheter 29 to perform an electro-anatomical mapping of a heart 23 of a patient 25. Catheter 29 comprises, at its distal end, one or more arms 20, which may be mechanically flexible, each of which is coupled with one or more electrodes 22. During the mapping procedure, electrodes 22 acquire and/or inject signals from and/or to the tissue of heart 23. A processor 28 receives these signals via an electrical interface 35, and uses information contained in these signals to construct an electro-anatomical map 31, which processor 28 saves in a memory 33 for further use, for example, to create the disclosed spatiotemporal electro-anatomical map, as described below. During and/or following the procedure, processor 28 may display electro-anatomical map 31 on a display 26.

During the procedure, a tracking system is used to track the respective locations of sensing-electrodes 22, such that each of the signals may be associated with the location at which the signal was acquired. For example, the Active Current Location (ACL) system, made by Biosense-Webster (Irvine Calif.), which is described in U.S. Pat. No. 8,456,182, whose disclosure is incorporated herein by reference, may be used. In the ACL system, a processor estimates the respective locations of the electrodes based on impedances measured between each of the sensing-electrodes 22, and a plurality of surface-electrodes 24, that are coupled to the skin of patient 25. For example, three surface-electrodes 24 may be coupled to the patient's chest, and another three surface-electrodes may be coupled to the patient's back. (For ease of illustration, only one surface-electrode is shown in FIG. 1.) The processor associates any given impedance signal received from electrodes 22 with the location in heart 23 at which the signal was acquired.

The example illustration shown in FIG. 1 is chosen purely for the sake of conceptual clarity. Other tracking methods can be used, such as ones based on measuring voltage signals, as with the Carto®4 system (produced by Biosense Webster). Other types of sensing catheters, such as the Lasso® Catheter (produced by Biosense Webster), may equivalently be employed. Contact sensors may be fitted at the distal end of electro-anatomical catheter 29. As noted above, other types of electrodes, such as those used for ablation, may be utilized in a similar way, fitted to electrodes 22 for acquiring the needed position data. Thus, an ablation electrode used for collecting position data is regarded, in this case, as a sensing-electrode. In an optional embodiment, processor 28 is further configured to indicate the quality of physical contact between each of the electrodes 22 and an inner surface of the cardiac chamber during measurement.

Processor 28 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 28 runs a dedicated algorithm as disclosed herein, including in FIG. 4, that enables processor 28 to perform the disclosed steps, as further described below.

Using Different Timing Pattern Displays of Different Cardiac Rhythms

FIGS. 2A-2C are schematic, illustrative scatterplots of local heart beat timing patterns, in accordance with an embodiment of the present invention. All three figures plot a "present" time period, i.e., cycle length, against an immediately preceding, or "previous," time period.

FIG. 2A is a timing pattern plot for a location over tissue that operates in a regular fashion, e.g., in a normal sinus rhythm. As seen, the timing pattern plot essentially gives one point 46a, since present and previous cycle lengths between EP activation are very similar in normal cardiac tissue.

FIG. 2B is a timing pattern plot for a location over tissue that exhibits arrhythmia of a particular type, named "type 1." As seen, "type 1" arrhythmia is characterized by a single value change 46b between consecutive cycle lengths.

FIG. 2C is a timing pattern plot for another location over tissue that exhibits another type of arrhythmia, named "type 2." As seen, "type 2" arrhythmia is characterized by the cycle length changing in a more complex fashion, i.e., between three values 46c. As further seen, each type of time-pattern is graphically encoded by assigning each respective location with a spatial footprint comprising graphical patterns 44a, 44b, and 44c, according to their respective types of timing pattern plots (i.e., classifying each location as either normal or arrhythmic with one type or other of arrhythmia showing at the location).

The example illustrations shown in FIGS. 2A-2C are chosen purely for the sake of conceptual clarity. FIGS. 2A-2C shows only parts relevant to embodiments of the present invention. For example, some variation may occur in the scatter plots, in a form of a broadening "cloud" about each point. Additional data processing steps, such as thresholding of heart beat wander may be applied to minimize inconclusive broadened timing pattern plots. In alternative embodiments, other classifications may be established, such as those that quantify the timing pattern seen in a scatter plot.

FIG. 3 is a schematic, pictorial illustration of a spatiotemporal electro-anatomical map 40 of a cardiac chamber, in accordance with an embodiment of the present invention. To produce map 40, the processor overlays the classified locations on an anatomical map of the cardiac chamber, such as on map 31. As seen, each region in map 40 may comprise one or more locations according to a legend 60: encoded to show a regular pattern, i.e., a region 52; encoded to show type 1 arrhythmia, i.e., a region 54; or encoded to show type 2 arrhythmia, i.e., a region 56. The locations of the different timing patterns plotted on an anatomical map create a spatiotemporal map of the cardiac chamber, and this map can assist the physician in locating an origin of an arrythmia and/or indicate an arrythmia type. Therefore, the disclosed technique provides physician 27 a clear visual representation of normal versus aberrant regions of a cardiac chamber tissue, so as to facilitate, for example, a decision on a required course of treatment.

The example illustration shown in FIG. 3 is chosen purely for the sake of conceptual clarity. In alternative embodiments, additional or alternative graphical elements, such as arrows with a variable length to quantify the timing pattern seen in a scatter plot, may be overlaid on map 31 to create map 40 based on the different classifications.

Figure 4:
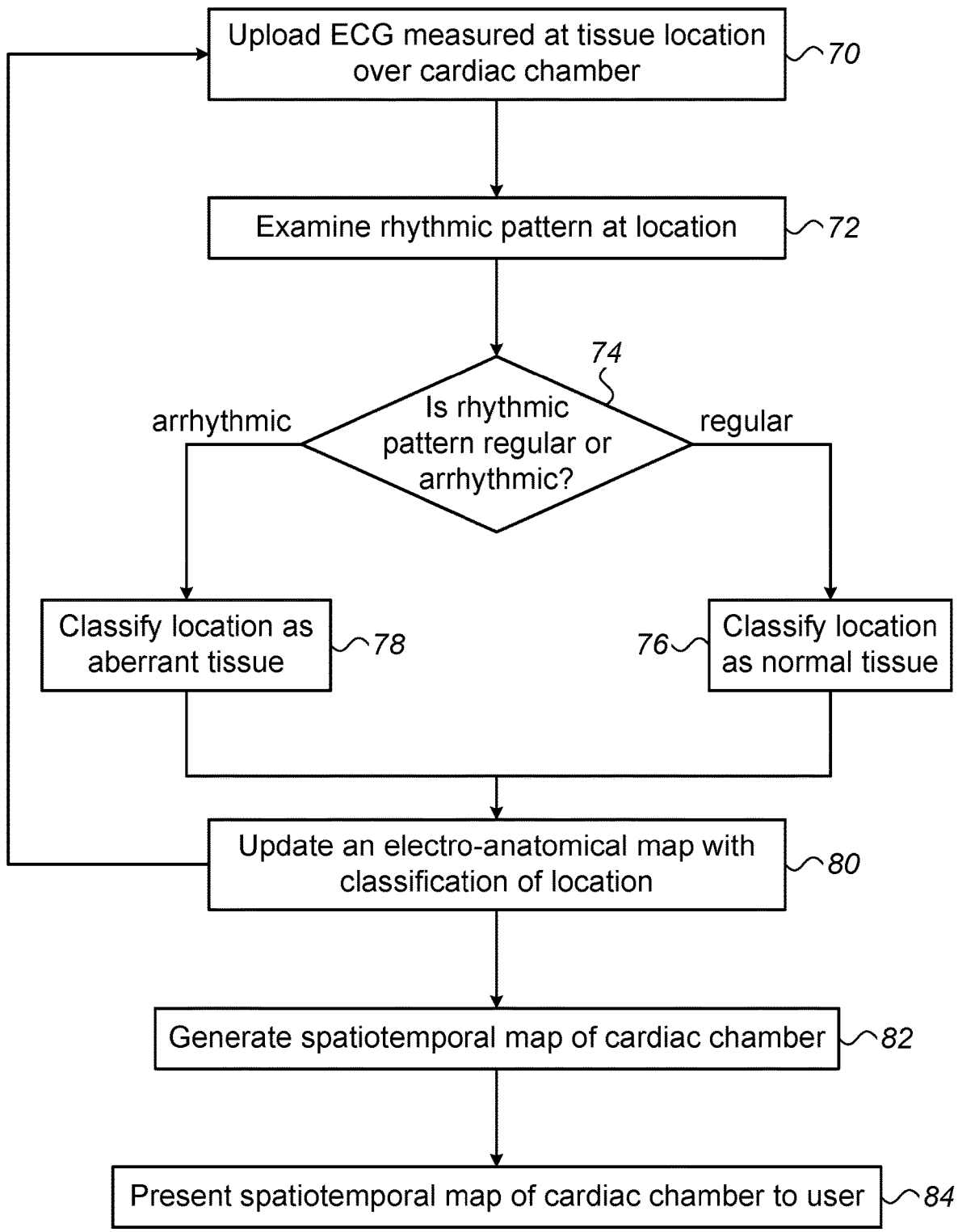
FIG. 4 is a flow chart that schematically illustrates a method and algorithm for a method for creating a spatiotemporal electro-anatomical map of a cardiac chamber, in accordance with an embodiment of the present invention.

FIG. 4 is a flow chart that schematically illustrates a method and algorithm for creating a spatiotemporal electro-anatomical map of a cardiac chamber, in accordance with an embodiment of the present invention. The algorithm, according to the present embodiment, carries out a process that begins with physician 30 uploading, from a memory 33, an intra-cardiac ECG trace that was measured at a location over an inner surface tissue of a cardiac chamber, at an ECG trace uploading step 70. Next, processor 28 examines the rhythmic pattern exhibited in the ECG trace, by processor 28 comparing timing patterns at the location, at a timing pattern checking step 72. In an analysis step 74, using the dedicated algorithm, processor 28 determines whether the analyzed rhythmic pattern is regular (i.e. repeatable) or aberrant (i.e., highly variable). Then, processor 28 classifies the tissue location accordingly as either normal or aberrant, at location classification steps 76 and 78, respectively.

At a next step, processor 28 updates an electro-anatomical map with the classified location, at an electro-anatomical map updating step 80. The process then loops to step 70 to examine another tissue location.

Finally, based on classifying the examined locations, processor 28 constructs spatiotemporal map 40 of the cardiac chamber tissue, by graphically encoding rhythmic pattern, as described in FIG. 3, at a spatiotemporal mapping step 82. The resulting spatiotemporal map is indicative of locations showing an arrhythmic activity. Finally, processor 28 presents the derived spatiotemporal map to physician 27, at a spatiotemporal map presentation step 84.

The example flow chart shown in FIG. 4 is chosen purely for the sake of conceptual clarity. Additional steps, such as presenting the arrhythmic timing patterns, are omitted from the purposely highly simplified flow chart.

Although the embodiments described herein mainly address cardiac applications, the methods and systems described herein can also be used in other applications, such as in electroencephalogram (EEG) based mapping of EP activity of a brain.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:
1. A method, comprising:
receiving an electrocardiogram (ECG) measured at a given location over a portion of a heart;
based on the measured ECG, identifying a rhythmic pattern over a given time-interval, the rhythmic pattern corresponding to a relation between a present cardiac cycle length and a preceding cardiac cycle length; and
based on the identified rhythmic pattern, determining a classification of the location as either showing regular rhythmic pattern or showing arrhythmia;
graphically encoding the location according to the classification by applying a first graphical pattern in response to the location being classified as showing a regular rhythmic pattern and applying a second graphical pattern, different from the first graphical pattern, in response to the location being classified as showing arrhythmia; and
overlaying the graphically encoded location on an anatomical map of the portion of a heart.

2. The method according to claim 1, wherein identifying the rhythmic pattern comprises calculating a difference between the present cardiac cycle length and the preceding cardiac cycle length.

3. The method according to claim 1, wherein classifying the location as showing arrhythmia comprises classifying a type of the arrhythmia.

4. The method according to claim 1, wherein overlaying the graphically encoded location comprises generating a spatiotemporal electro-anatomical map of the portion of a heart.

5. The method according to claim 1, and comprising measuring the ECG using a catheter-based system for electro-anatomical mapping.

6. A system, comprising:
a memory, which is configured to store an electrocardiogram (ECG) measured at a given location over a portion of a heart; and
a processor, which is configured to:
based on the measured ECG, identify a rhythmic pattern over a given time-interval, the rhythmic pattern corresponding to a relation between a present cardiac cycle length and a preceding cardiac cycle length; and
based on the identified rhythmic pattern, determine a classification of the location as either showing regular rhythmic pattern or showing arrhythmia;
graphically encode the location according to the classification by applying a first graphical pattern in response to the location being classified as showing a regular rhythmic pattern and applying a second graphical pattern, different from the first graphical pattern, in response to the location being classified as showing arrhythmia; and
overlay the graphically encoded location on an anatomical map of the portion of a heart.

7. The system according to claim 6, wherein the processor is configured to identify the rhythmic pattern by calculating a difference between the present cardiac cycle length and the preceding cardiac cycle length.

8. The system according to claim 6, wherein the processor is configured to classify the location as showing arrhythmia by classifying a type of the arrhythmia.

9. The system according to claim 5, wherein the processor is configured to overlay the graphically encoded location by generating a spatiotemporal electro-anatomical map of the portion of a heart.

10. The system according to claim 5, wherein the system is further configured to measure the ECG using a catheter-based system for electro-anatomical mapping.

* * * * *